United States Patent
Lefkowitz

(10) Patent No.: US 11,400,046 B2
(45) Date of Patent: *Aug. 2, 2022

(54) PROBIOTIC CONFECTION AND LIPID COMPOSITIONS

(71) Applicant: Ganeden Biotech, Inc., Mayfield Heights, OH (US)

(72) Inventor: Andrew R. Lefkowitz, Mayfield Heights, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/209,953

(22) Filed: Dec. 4, 2018

(65) Prior Publication Data
US 2019/0307679 A1    Oct. 10, 2019

Related U.S. Application Data

(60) Continuation of application No. 15/464,019, filed on Mar. 20, 2017, now Pat. No. 10,143,649, which is a division of application No. 15/090,086, filed on Apr. 4, 2016, now Pat. No. 9,597,286, which is a continuation of application No. 13/086,675, filed on Apr. 14, 2011, now Pat. No. 9,301,982.

(60) Provisional application No. 61/390,355, filed on Oct. 6, 2010, provisional application No. 61/323,914, filed on Apr. 14, 2010.

(51) Int. Cl.

| | | |
|---|---|---|
| A61K 9/00 | (2006.01) | |
| A23L 33/135 | (2016.01) | |
| A61K 35/744 | (2015.01) | |
| A61K 35/742 | (2015.01) | |
| A61K 31/202 | (2006.01) | |
| A61K 35/612 | (2015.01) | |
| A23D 9/007 | (2006.01) | |
| A23G 1/42 | (2006.01) | |
| A23G 1/54 | (2006.01) | |
| A23G 3/34 | (2006.01) | |
| A23G 3/36 | (2006.01) | |
| A23G 3/44 | (2006.01) | |
| A23G 3/54 | (2006.01) | |
| A61K 35/745 | (2015.01) | |
| A61K 35/747 | (2015.01) | |
| A61K 9/48 | (2006.01) | |
| A61K 36/02 | (2006.01) | |
| A61K 35/00 | (2006.01) | |

(52) U.S. Cl.
CPC ............ *A61K 9/0056* (2013.01); *A23D 9/007* (2013.01); *A23G 1/423* (2013.01); *A23G 1/54* (2013.01); *A23G 3/343* (2013.01); *A23G 3/366* (2013.01); *A23G 3/44* (2013.01); *A23G 3/54* (2013.01); *A23L 33/135* (2016.08); *A61K 9/48* (2013.01); *A61K 31/202* (2013.01); *A61K 35/612* (2013.01); *A61K 35/742* (2013.01); *A61K 35/744* (2013.01); *A61K 35/745* (2013.01); *A61K 35/747* (2013.01); *A61K 36/02* (2013.01); *A23V 2002/00* (2013.01); *A61K 2035/115* (2013.01)

(58) Field of Classification Search
CPC .... A61K 35/74; A61K 35/742; A61K 35/612; A61K 35/744; A61K 35/745; A61K 9/0056; A61K 9/48; A23G 3/366; A23L 33/135

See application file for complete search history.

(56) References Cited

U.S. PATENT DOCUMENTS

| | | | |
|---|---|---|---|
| 4,110,477 | A | 8/1978 | Naruse et al. |
| 4,323,651 | A | 4/1982 | Long et al. |
| 4,980,180 | A | 12/1990 | Cully et al. |
| 5,079,164 | A | 1/1992 | Kirkovits et al. |
| 5,102,800 | A | 4/1992 | Hirikoshi |
| 5,200,336 | A | 4/1993 | Kong et al. |
| 5,928,664 | A | 7/1999 | Yang et al. |
| 6,368,580 | B1 | 4/2002 | Bondi et al. |
| 6,461,607 | B1 | 10/2002 | Farmer |
| 6,531,126 | B2 | 3/2003 | Farmer |
| 6,645,506 | B1 | 11/2003 | Farmer |
| 6,716,435 | B1 | 4/2004 | Farmer et al. |
| 6,723,326 | B1 | 4/2004 | Farmer |
| 6,733,751 | B2 | 5/2004 | Farmer |
| 6,811,786 | B1 | 11/2004 | Farmer et al. |
| 6,849,256 | B1 | 2/2005 | Farmer |
| 6,905,692 | B2 | 6/2005 | Farmer |
| 7,025,974 | B2 | 4/2006 | Farmer et al. |
| 7,048,950 | B2 | 5/2006 | Farmer |
| 7,232,571 | B2 | 6/2007 | Farmer et al. |

(Continued)

FOREIGN PATENT DOCUMENTS

| | | |
|---|---|---|
| AU | 2017201392 A1 | 3/2017 |
| CA | 2606495 A1 | 11/2006 |

(Continued)

OTHER PUBLICATIONS

King'U, "Colony Forming Units (CFU)" http://www.moldbacteriaconsulting.com/fungi/colony-forming-units-cfu.html, 2020 (Year: 2020).*

(Continued)

*Primary Examiner* — Ruth A Davis

(74) *Attorney, Agent, or Firm* — Sughrue Mion, PLLC

(57) ABSTRACT

The present application relates to probiotic confection-based compositions comprising lactic acid-producing bacteria and oil-based compositions comprising the same.

9 Claims, No Drawings

(56) References Cited

U.S. PATENT DOCUMENTS

| | | |
|---|---|---|
| 7,371,407 B2 | 5/2008 | Farmer |
| 7,507,402 B1 | 3/2009 | Farmer et al. |
| 7,541,042 B2 | 6/2009 | Farmer |
| 7,544,363 B2 | 6/2009 | Farmer |
| 7,700,093 B2 | 4/2010 | Farmer et al. |
| 7,708,988 B2 | 5/2010 | Farmer |
| 7,713,726 B2 | 5/2010 | Farmer |
| 7,767,203 B2 | 8/2010 | Farmer et al. |
| 7,807,151 B2 | 10/2010 | Farmer |
| 7,807,185 B2 | 10/2010 | Farmer |
| 7,854,927 B2 | 12/2010 | Farmer et al. |
| 8,097,247 B2 | 1/2012 | Farmer |
| 8,187,590 B2 | 5/2012 | Farmer |
| 8,273,346 B2 | 9/2012 | Farmer et al. |
| 8,277,799 B2 | 10/2012 | Farmer |
| 8,343,484 B2 | 1/2013 | Farmer et al. |
| 8,349,337 B1 | 1/2013 | Farmer et al. |
| 8,409,591 B2 | 4/2013 | Farmer et al. |
| 8,568,743 B2 | 10/2013 | Farmer et al. |
| 8,568,744 B2 | 10/2013 | Farmer et al. |
| 8,697,055 B2 | 4/2014 | Farmer |
| 8,821,854 B2 | 9/2014 | Farmer et al. |
| 9,192,659 B2 | 11/2015 | Farmer et al. |
| 9,220,736 B2 | 12/2015 | Farmer et al. |
| 9,301,982 B2 | 4/2016 | Lefkowitz |
| 9,446,111 B2 | 9/2016 | Farmer et al. |
| 9,597,286 B2 | 3/2017 | Lefkowitz |
| 9,622,502 B2 | 4/2017 | Farmer et al. |
| 9,895,310 B2 | 2/2018 | Lefkowitz |
| 10,143,649 B2 * | 12/2018 | Lefkowitz ............... A23D 9/007 |
| 2003/0031659 A1 | 2/2003 | Farmer |
| 2005/0232909 A1 | 10/2005 | Farmer |
| 2006/0099321 A1 | 5/2006 | Sievert |
| 2006/0188607 A1 * | 8/2006 | Schramm ............... A23D 7/005 |
| | | 426/72 |
| 2007/0269577 A1 | 11/2007 | Pershad et al. |
| 2008/0038240 A1 | 2/2008 | Farmer et al. |
| 2008/0166449 A1 | 7/2008 | Kabse et al. |
| 2008/0206212 A1 | 8/2008 | McMahon et al. |
| 2008/0274153 A1 | 11/2008 | Farmer |
| 2009/0130179 A1 * | 5/2009 | Lakkis .................... A23G 3/36 |
| | | 424/440 |
| 2009/0186057 A1 | 7/2009 | Farmer et al. |
| 2009/0186126 A1 | 7/2009 | Farmer et al. |
| 2009/0232941 A1 | 9/2009 | Farmer |
| 2010/0210000 A1 | 8/2010 | Farmer et al. |
| 2011/0195154 A1 | 8/2011 | Farmer |
| 2011/0217275 A1 | 9/2011 | Opheim |
| 2011/0256216 A1 | 10/2011 | Lefkowitz |
| 2011/0274676 A1 | 11/2011 | Farmer et al. |
| 2012/0251512 A1 | 10/2012 | Farmer et al. |
| 2013/0164398 A1 | 6/2013 | Farmer |
| 2013/0195824 A1 | 8/2013 | Farmer et al. |
| 2013/0216577 A1 | 8/2013 | Farmer et al. |
| 2013/0251695 A1 | 9/2013 | Farmer et al. |
| 2013/0344046 A1 | 12/2013 | Farmer et al. |
| 2014/0242051 A1 | 8/2014 | Farmer |
| 2015/0044317 A1 | 2/2015 | Farmer et al. |
| 2015/0313951 A1 | 11/2015 | Cash et al. |
| 2016/0213612 A1 | 7/2016 | Lefkowitz |
| 2016/0213613 A1 | 7/2016 | Lefkowitz |
| 2016/0213614 A1 | 7/2016 | Lefkowitz |
| 2016/0213615 A1 | 7/2016 | Lefkowitz |
| 2017/0000872 A1 | 1/2017 | Farmer et al. |
| 2017/0035813 A1 | 2/2017 | Farmer et al. |
| 2017/0189331 A1 | 7/2017 | Lefkowitz |
| 2017/0189457 A1 | 7/2017 | Farmer et al. |

FOREIGN PATENT DOCUMENTS

| | | |
|---|---|---|
| WO | WO-2006007470 A1 | 1/2006 |
| WO | WO-2009102575 A1 | 8/2009 |

OTHER PUBLICATIONS

ATCC Catalogue of Bacteria and Bacteriophages, Accession No. 31284, retrieved Aug. 11, 2009.

Nakamura et al., Taxonomic Study of Bacillus coagulans Hammer 1915 with a Proposal for *Bacillus smithii* sp. Nov. Int. J. Syst. Bateriol. 1988;38(1):63-73.

Sneath et al., eds., Bergey's Manual of Systematic Bacteriology, Williams & Wilkins, Baltimore, MD, 2:1122-1132 (1986).

Nakamura et al., "Taxonomic Study of *Bacillus coagulans* Hammer 1915 with a Proposal for *Bacillus smithii* sp. Nov.", *Int. J. Syst. Bateriol.*, 38(1):63-73 (1988).

Barrile et al., Microflora of cocoa beans before and after roasting at 150 C. J Milk Food Technol. 1971;34(7):369-71.

* cited by examiner

PROBIOTIC CONFECTION AND LIPID COMPOSITIONS

RELATED APPLICATIONS

This application is a Continuation of application Ser. No. 15/464,019 filed on Mar. 20, 2017 now U.S. Pat. No. 10,143,649, issued Dec. 4, 2018, which is a divisional of U.S. Ser. No. 15/090,086, filed Apr. 4, 2016, now U.S. patent Ser. No. 9/597,286, issued Jul. 28, 2016, which is a continuation of U.S. Ser. No. 13/086,675, filed Apr. 14, 2011, now U.S. Pat. No. 9,301,982, issued Apr. 5, 2016, claiming the benefit of priority to U.S. Provisional Patent Application No. 61/390,355, filed Oct. 6, 2010 and U.S. Provisional Patent Application No. 61/323,914, filed on Apr. 14, 2010, the entire contents of each of which are incorporated herein by reference in their entireties.

FIELD OF THE INVENTION

The present application relates to probiotic confection and lipid compositions comprising lactic acid-producing bacteria.

BACKGROUND OF THE INVENTION

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. These findings have led to attempts to modify the composition and metabolic activities of the bacterial community through diet, primarily with probiotics, which are live microbial food supplements.

Probiotic organisms are non-pathogenic, non-toxigenic, retain viability during storage, and typically survive passage through the stomach and small intestine. Since probiotics do not generally permanently colonize the host, they need to be ingested regularly for health promoting properties to persist.

SUMMARY OF THE INVENTION

The invention is based on the discovery that lactic acid-producing bacteria, particularly *Bacillus* species, remain viable and retain their beneficial probiotic properties in/on confection-based compositions as well as lipid or oil-based compositions. Accordingly, the invention describes probiotic confection-based compositions and seafood/fish oil soft-gels or capsules. Specifically, the invention provides an isolated *Bacillus coagulans* in such compositions. The compositions are suitable for human or animal consumption.

The invention provides probiotic confection-based compositions comprising a confection and an isolated *Bacillus coagulans* bacterium. The *Bacillus coagulans* bacterium is coated on the exterior surface of the confection. Alternatively, the *Bacillus coagulans* bacterium is inside the confection itself. For example, the bacterium is incorporated throughout the confection. Optionally, the composition further comprises a granulated or powder sugar coating or dusting on the exterior surface of the confection. For example, a sugar-sanded jelly confection is characterized by a flexible candy base structure and a sugar sanding layer or coating that comprises *B. coagulans* spores or vegetative cells in an admixture with a granulated or powdered sugar or other sweetener.

Suitable confections include hard sweets, fudge, toffee, liquorice, chocolate, jelly candy, marshmallow, and marzipan. Preferably, the jelly candy is a gelatin-based gummi candy. Exemplary gummi candies include gummi bears, gummi worms, gummi frogs, gummi hamburgers, gummi cherries, gummi soda bottles, gummi sharks, gummi army men, gummi hippopotami, gummi lobsters, gummi watermelons, gummi octopuses, gummi apples, gummi peaches, and gummi oranges. Preferably, the probiotic confection-based composition is a gummi bear with isolated *Bacillus coagulans* coated on the external surface. The terms "gummi" and "gummy" are used interchangeably herein.

In one aspect, the isolated *Bacillus coagulans* comprise between about 0.01% to about 50% by weight of the confection-based composition. Optionally, the isolated *Bacillus coagulans* comprise between about 0.01% and about 10% by weight of the confection-based composition. Preferably, the isolated *Bacillus coagulans* comprise between about 0.01% and about 5% by weight of the confection-based composition, e.g., about 1%, about 2%, about 3%, about 4%, or about 5% by weight of the confection-based composition.

The invention also provides bacterial species including *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC$^{30}$, ATCC Designation Number PTA-6086; and GBI-40, ATCC Designation Number PTA-6087; see U.S. Pat. No. 6,849,256 to Farmer).

Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores. The *Bacillus coagulans* is predominantly in spore form, e.g., about 75%, about 80%, about 85%, about 90%, about 95%, about 99%, or about 100% spores. Alternatively, the *Bacillus coagulans* is predominantly in vegetative form, e.g., about 75%, about 80%, about 85%, about 90%, about 95%, about 99%, or about 100% vegetative cells.

The invention provides compositions comprising a dry mix for confection-based compositions comprising sugar and an isolated *Bacillus coagulans* bacterium. The dry mix is between 1% and 50% *Bacillus coagulans* bacterium, e.g., about 5%, about 10%, about 15%, about 20%, about 25%, about 35%, about 45%, or about 50% *Bacillus coagulans* bacterium. Preferably, the dry mix is about 15% *Bacillus coagulans* bacterium. For example, about 100 pounds of dry mix contains about 15 pounds of *Bacillus coagulans* bacterium and about 85 pounds of sugar.

The dry mix is between about 1% and about 50% by weight of the confection-based composition, e.g., about 1% to about 20%, about 5% to about 15%; about 6%, about 7%, about 8%, about 9%, or about 10% by weight of the confection-based composition. For example, a 3 gram confection-based composition contains about 7% dry mix by weight of the confection-based composition. A 3.8 to 4 gram confection-based composition contains about 8-9% dry mix by weight of the confection-based composition.

The invention also provides methods of making a probiotic confection-based composition. First, a confection (e.g., a gummi bear) is provided and heated to about 100° C. to make the confection "sticky". Subsequently, isolated *Bacillus coagulans* bacterium and sugar are applied to an external surface of the confection, thereby making a probiotic confection-based composition. Preferably, the confection is a gummi bear. The isolated *Bacillus coagulans* comprise between 1% and 10% by weight of the confection-based composition. In one aspect, the isolated *Bacillus coagulans* is *Bacillus coagulans* hammer strain Accession No. ATCC 31284. The isolated *Bacillus coagulans* is selected from the group consisting of GBI-30 strain (ATCC Designation Number PTA-6086), GBI-20 strain (ATCC Designation Number PTA-6085), and GBI-40 strain (ATCC Designation Number PTA-6087). Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores.

*Bacillus coagulans* bacteria are included in the confection-based compositions of this invention. Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or $BC^{30}$, ATCC Designation Number PTA-6086; and GBI-40, ATCC Designation Number PTA-6087; see U.S. Pat. No. 6,849,256 to Farmer).

The invention also provides a probiotic seafood/fish oil-based composition comprising fish oil and an isolated *Bacillus coagulans* bacterium. For example, the fish oil, e.g., salmon, cod (e.g., cod liver) contains omega-3 fatty acids. Alternatively, the oil is omega-3 fatty acid krill oil. The oil comprises eicosapentaenoic acid or docosahexaenoic acid. The composition is encapsulated in as soft-shelled capsule or a soft gelatin capsule. Alternatively, the composition is a gelatin-based gummi candy. In one aspect, the isolated *Bacillus coagulans* comprise between 0.01% and 10% by weight of the composition, e.g., about 1% to about 10%; about 2% to about 9%; or about 5% to about 8% by weight of the composition.

In some cases, the isolated *Bacillus coagulans* is in the form of a mixture of vegetative cells and spores. Preferably, the isolated *Bacillus coagulans* is in the form of a spore. More preferably, the bacterium is present as at least 90% spores, e.g., 95%, 98%, or 99% spores. The isolated *Bacillus coagulans* is selected from the group consisting of GBI-30 strain (ATCC Designation Number PTA-6086), GBI-20 strain (ATCC Designation Number PTA-6085), and GBI-40 strain (ATCC Designation Number PTA-6087).

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION OF THE INVENTION

Probiotic organisms are non-pathogenic, non-toxigenic, retain viability during storage, and survive passage through the stomach and small intestine. Non-pathogenic lactic acid-producing bacteria (i.e., "lactic acid bacteria"), such as the exemplary *Bacillus coagulans*, remain viable and retain their beneficial probiotic properties in confection-based compositions, such as those prepared in boiling water. Specifically, the probiotic organisms described herein, e.g., *Bacillus coagulans* strain GBI-30 or $BC^{30}$, ATCC Designation Number PTA-6086, survive the harsh manufacturing processes of the confection-based compositions described below.

Probiotic Lactic Acid-Producing Bacteria

A probiotic lactic acid-producing bacteria suitable for use in the methods and compositions of the invention produces acid and is non-pathogenic. Purified and/or isolated *Bacillus coagulans* is particularly useful as a probiotic in the compositions described herein. By "purified" or "substantially purified" is meant a *Bacillus coagulans* bacterium that is substantially free of contaminating microorganisms or other macromolecules, e.g., polysaccharides, nucleic acids, or proteins.

The confection-based compositions include a lactic acid-producing bacteria, such as a spore-forming *Bacillus* species, such as *B. coagulans*. Preferably, the spore-forming *Bacillus* species of the invention is *B. coagulans* Hammer. There are many suitable bacteria identified as described herein, although the invention is not limited to currently known bacterial species insofar as the purposes and objectives of the bacteria is described. The property of acid production is important to the effectiveness of the probiotic lactic acid-producing bacteria of this invention.

Exemplary methods and compositions are described herein using *Bacillus coagulans* as a probiotic. Purified and/or isolated *Bacillus coagulans* is particularly useful as a probiotic in confection-based compositions. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art.

*Bacillus coagulans* is a non-pathogenic gram positive spore-forming bacteria that produces L(+) lactic acid (dextrorotatory) in fermentation conditions. It has been isolated from natural sources, such as heat-treated soil samples inoculated into nutrient medium (Bergey's Manual off Systemic Bacteriology, Vol. 2, Sneath, P. H. A., et al., eds., Williams & Wilkins, Baltimore, Md., 1986). Purified *B. coagulans* strains have served as a source of enzymes including endonucleases (e.g., U.S. Pat. No. 5,200,336); amylase (U.S. Pat. No. 4,980,180); lactase (U.S. Pat. No. 4,323,651); and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 (BC$^{30}$), ATCC Designation Number PTA-6086; and GBI-40, ATCC Designation Number PTA-6087; see U.S. Pat. No. 6,849,256 to Farmer).

*Bacillus coagulans* was previously mis-characterized as a *Lactobacillus* and labeled as *Lactobacillus sporogenes* (Nakamura et al. 1988. *Int. J. Syst. Bacteriol.* 38: 63-73). However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic *Lactobacillus* species are unsuitable for colonization of the gut due to their instability in the harsh (i.e., acidic) pH environment of the bile, particularly human bile. By contrast, *Bacillus coagulans* is able to survive and colonize the gastrointestinal tract in the bile environment and even grown in this low pH range.

Probiotic Activity of *Bacillus coagulans*

It is well-documented clinically that many species of bacterial, mycotic and yeast pathogens possess the ability to cause a variety of gastrointestinal disorders including, but not limited to: disruption of normal gastrointestinal biochemical function, necrosis of gastrointestinal tissues, and disruption of the bioabsorption of nutrients, and like conditions. The probiotic microorganism-containing compositions described herein inhibit these pathogens. Thus, the compositions are useful in the prophylactic or therapeutic treatment of conditions associated with infection by these aforementioned pathogens. The probiotic confection-based compositions of the invention are also used in the methods described herein for boosting the immune system.

In one aspect, a *Bacillus coagulans* strain is included in the composition in the form of vegetative cells. In another aspect, the *Bacillus coagulans* strain is included in the composition in the form of spores. The invention also provides for including the *Bacillus coagulans* strain in the composition in the form of a powder, a dried cell mass, a stabilized paste, or a stabilized gel.

Because *Bacillus* spores are heat and pressure-resistant and can be stored as a dry powder, they are particularly useful for formulation into and manufacture of products such as the various confection-based compositions described herein. A *Bacillus* species is well suited for the present invention, particularly species having the ability to form spores which are relatively resistant to heat and other conditions, making them ideal for storage (shelf-life) in product formulations, e.g., confection-based compositions. Due to the shelf-stable properties of the *Bacillus coagulans* strains described herein, e.g., *Bacillus coagulans* strain GBI-30 or BC$^{30}$, ATCC Designation Number PTA-6086, the product formulations of the invention are not confined to a refrigerator and may be stored at room temperature.

The *Bacillus coagulans* of the invention survives storage (shelf-life) from about 12 days to about 2 years; from about 1 month to about 18 months; from about 3 months to about 1 year; or from about 6 months to about 9 months.

The probiotic organisms described herein, e.g., *Bacillus coagulans* strain GBI-30 or BC$^{30}$, ATCC Designation Number PTA-6086, promote digestive and oral health and support the immune system. The ability of *Bacillus coagulans* to inhibit various bacterial pathogens was quantitatively ascertained by use of an in vitro assay. This assay is part of a standardized bacterial pathogen screen (developed by the U.S. Food and Drug Administration (FDA)) and is commercially available on solid support disks (DIFCO® BACTROL® Antibiotic Disks). To perform the assay, potato-dextrose plates (DIFCO®) were initially prepared using standard procedures. The plates were then individually inoculated with the bacteria (approximately 1.5×10$^6$ CFU) to be tested so as to form a confluent bacterial bed.

Inhibition of microorganisms (e.g. gastrointestinal pathogens) by *Bacillus coagulans* was subsequently ascertained by placing approximately 1.8×10$^6$ CFU of *Bacillus coagulans* in 10 µl of broth or buffer, directly in the center of the potato-dextrose plate with one test locus being approximately 8 mm in diameter per plate. A minimum of three test loci were used for each assay. The negative control consisted of a 10 µl volume of a sterile saline solution, whereas the positive control consisted of a 1 µl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) *Clostridium* species—excellent inhibition; (ii) *Escherichia coli*—excellent inhibition; (iii) *Clostridium* species—excellent inhibition, where the zone of inhibition was consistently greater than 15 mm in diameter. Similarly, excellent inhibition was also seen for the opportunistic pathogens *Pseudornonas aeruginosa*, and *Staphylococcus aureus*. Pathogenic enteric bacteria which were inhibited by *Bacillus coagulans* activity include, but are not limited to: *Staphylococcus aureus; Staphylococcus epidermidis; Streptococcus pyogenes; Pseudomonas aeruginosa; Escherichia coli* (enterohemorragic species); numerous *Clostridium* species (e.g., *Clostridium perfingens, Clostridium botulinum, Clostridium tributrycum, Clostridium sporogenes*, and the like); *Gardnereia vaginails; Proponbacterium aenes; Aeromonas hydrophia; Aspergillus* species; *Proteus* species; and *Klebsiella* species.

Micro-Encapsulation

In one aspect, the lactic-acid producing bacteria are incorporated into a microcapsule coating prior to addition to the confection-based composition, using any micro-encapsulation process well-known in the art. The isolated *Bacillus coagulans* are packaged, or encapsulated, within another material in order to protect the bacteria from the surrounding environment. The capsules of the invention range in size from one-thousandth of a millimeter to seven millimeters. The internal ingredients of the microcapsule are released from their shells in various ways, including mechanical rupture of the capsule wall, dissolution of the wall, melting of the wall and diffusion through the wall. Thus, micro-encapsulation provides additional protection to the isolated *Bacillus* bacterium during heat processing of the confection-based compositions of the invention. Physical methods of micro-encapsulation include pan coating, air-suspension coating, centrifugal extrusion, vibrational nozzle, and spray-drying. Chemical methods of micro-encapsulation include interfacial polymerization, in-situ polymerization, and matrix polymerization.

Alternatively, the lactic-acid producing bacteria is added to the confection-based composition without micro-encapsulation.

Probiotic Confection-Based Compositions

The invention is directed to the surprising discovery that lactic acid-producing bacteria, particularly *Bacillus* species, remain viable and retain their beneficial probiotic properties in confection-based compositions. The confection compositions are suitable for human or animal consumption. In one aspect, the confection-based compositions are administered to children under 18 years of age, e.g., under 15 years of age, under 10 years of age, or under 5 years of age. Alternatively, the confection-based compositions are administered to children and adults of all ages.

Confectionery includes food items that are rich in sugar or artificial sweeteners, any one or type of which is called a "confection". The words "candy" or "sweets" are also used for the term "confectionery". Candy is made by dissolving sugar in water or milk to form a syrup, which is boiled until it reaches the desired concentration or starts to caramelize. The type of candy depends on the ingredients and how long the mixture is boiled, while the final texture of candy depends on the sugar concentration. As the syrup is heated, it boils, water evaporates, the sugar concentration increases, and the boiling point rises. Thus, boiling temperature corresponds to a particular sugar concentration. In general, higher temperatures and greater sugar concentrations result in hard, brittle candies, while lower temperatures result in softer candies. Candy names come from the process used to test the syrup before thermometers became affordable: a small spoonful of syrup was dropped into cold water, and the characteristics of the resulting lump were evaluated to determine the concentration of the syrup. Long strings of hardened sugar indicate "thread" stage, while a smooth lump indicates "ball" stages, with the corresponding hardness described. The "crack" stages are indicated by a ball of candy so brittle that the rapid cooling from the water literally causes it to crack. Candy comes in an endless variety of textures from soft and chewy to hard and brittle.

There are a variety of categories and types of confectionery. Hard sweets are based on sugars cooked to the hard-crack stage, including suckers, lollipops, jawbreakers (or gobstoppers), lemon drops, peppermint drops and disks, candy canes, rock candy, etc. Hard sweets also include candies often mixed with nuts, such as brittle. Others contain flavorings including coffee, such as Kopiko. Fudge is a confection of milk and sugar boiled to the soft-ball stage. Toffee (or Taffy or Tuffy) is based on sugars cooked to the soft-ball stage and then pulled to create an elastic texture. Tablet is a crumbly milk-based soft and hard candy, based on sugars cooked to the soft-ball stage, and comes in several forms, such as wafers and heart shapes. Liquorice, which contains extract of the liquorice root, is chewier and more resilient than gum/gelatin candies, but still designed for swallowing. Other types of confection include chocolates, marshmallow, marzipan, and divinity. Jelly candies include those based on sugar and starch, pectin, gum, or gelatin, e.g., jelly beans, gumdrops, jujubes, cola bottles, and gummies.

Suitable gummi confections include bears, rings, worms, frogs, snakes, hamburgers, cherries, sharks, penguins, hippos, lobsters, octopuses, apples, peaches, oranges, and spiders. Suitable gummi bear sizes range from the standard candy size (or smaller), to gummi bears that weigh several kilograms. Gummi confections come in a variety of flavors, including raspberry, orange, strawberry, pineapple, and lemon.

Traditional gummi confection (e.g., gummi bears) is made from sugar, glucose syrup, starch, flavoring, food coloring, citric acid, and gelatin. Suitable gelling agents and hydrocolloids can be selected by one of ordinary skill in the art. Examples include gums, carrageenan, gelatin, pectin, high methoxy pectin, alginates, and agar. One of ordinary skill in the art can select a suitable gelling agent or hydrocolloid depending on the desired final texture of the starch molded piece. There are some gummi confections made with pectin or starch instead of gelatin, making them suitable for vegetarians. An exemplary organic gummi confection is made with most all natural ingredients, such as organic tapioca syrup, organic evaporated cane juice, gelatin, organic grape juice concentrate, citric acid, lactic acid, ascorbic acid, colors added (black, carrot juice concentrate, turmeric, annatto), natural flavors, organic sunflower oil, and carnauba wax.

Large sour gummi bears are larger and flatter than traditional gummi bears, have a softer texture, and include fumaric acid or other acid ingredients to produce a sour flavor. Sour "gummies" are produced by forming a sweet, flavored, and chewy core and subsequently dusting the exterior with a food acid, such as citric acid. The gelling ingredient in the core of these products is ordinarily gelatin or pectin. The acidic exterior is applied by use of a wetting agent or food adhesive. Some manufacturers produce sour bears with a different texture, based on starch instead of gelatin. Typically, starch produces a shorter (cleaner bite, less chewy) texture than gelatin.

Confection-based compositions, such as those described herein, are made from a variety of ingredients known to those skilled in the art. The confection-based compositions are prepared by combining confection ingredients and a liquid, e.g., water or milk. In one aspect, the composition is prepared by combining confection ingredients and a liquid, and heating the resulting combination. Optionally, the combination is heated (heat-processed) using applied heat, a flame, or a microwave. The confection-based composition is boiled in hot water, e.g., stovetop boiling, addition of boiling water to a container, or microwaving the confection-based composition along with water. In one aspect, boiling water (about 100° C.) is added to a combination of confection ingredients and *Bacillus coagulans* bacteria.

Mass production of gummi confection (e.g., gummi bears) includes mixing the gummi confection ingredients and pouring the resulting mixture into many starched-lined (e.g., corn starch-lined) trays/molds. The corn starch prevents the gummy bears from sticking to the mold and lets them release easily once they are set. First, the desired character molds are created and, if necessary, duplicated with a machine. Optionally, starch powder is applied to the character molds. Gummi confection ingredients, such as sugar, glucose syrup, gelatin, and water are mixed together and heated. In one aspect, the ingredients are mixed with colors and flavors that give the bears their signature look and taste. The molten gelatin mixture is poured into the molds and allowed to cool and set prior to packaging or consumption. Preferably, the gummi confection is subsequently heated and placed in a large drum tumbler to apply a composition of isolated *Bacillus coagulans* and a sweetener (e.g., a sugar).

More specifically, as described in WO/2009/102575, production of gummi confection includes the following. A colloid batch and a puree batch are formed and combined with corn syrup and sugar to form a base slurry. The colloid batch comprises a solution of the gelling agent in water at a level of from 5 to 15% by weight of the gelling agent, more preferably from 7 to 12% of the gelling agent based on the total weight of the colloid batch. The colloid batch is held at a temperature of 170 to 190° F. The puree batch preferably comprises water, fruit puree and/or high fructose corn syrup or other sweeteners, thin boiling starch, and sodium citrate. It is held at a temperature of from 65 to 75° F. Preferably, the fruit puree has a Brix of from 10 to 45, more preferably from 25 to 40. Optionally, the puree batch includes a plurality of fruit purees. The fruit puree comprises a typical fruit puree, a fruit juice, or a fruit powder. The puree batch comprises from 30 to 40% by weight water, from 0 to 40% by weight fruit puree, from 0 to 40% by weight high fructose corn syrup, from 25 to 35% by weight thin boiling starch, and from 0.0 to 2.0% by weight sodium citrate. In a mixing kettle from 25 to 40% by weight of additional corn syrup is combined with from 15 to 40% by weight of fine granulated sugar, from 10 to 15% by weight of the colloid batch and from 20 to 30% by weight of the puree batch to form the base slurry. Preferably, the corn syrup is approximately 42 DE corn syrup, however, as would be understood by one of ordinary skill in the art other DE corn syrups could be used. The base slurry components are completely mixed and held at 130 to 150° F. in a holding tank.

The base slurry is then cooked to bring the Brix to from 70 to 85 Brix, more preferably to a Brix of from 75 to 80. In one embodiment the base slurry is passed through a coil cooker and heated to a temperature of from 250 to 325° F. to cook it. Other cooking methods could be used as will be understood by one of ordinary skill in the art. The cooked base slurry is preferably subjected to vacuum to further increase the Brix into the desired range. The cooked base slurry is held at approximately 200° F. until used. An acidulant solution is preferably added along with color and flavor to the cooked base slurry just prior to deposition in the starch molds. In one aspect, the acidulant solution comprises ascorbic acid present in an amount of from 15 to 20% by weight, citric acid present in an amount of from 10 to 20% by weight, and malic acid present in an amount of from 5 to 10% by weight with the remainder comprising water. As would be understood by one of ordinary skill in the art, other edible acids could be used in place of or in addition to those listed. In one aspect, 95 to 97% by weight of cooked base slurry is combined with from 2 to 3% by weight of the acidulant solution and the remainder comprises flavors and colors. Optionally, the acidulant solution is used to bring the pH of the base slurry to from 2.6 to 3.2. One of ordinary skill in the art would have no difficulty selecting suitable colors and flavors. The combined mixture is then deposited into starch molds, e.g., using a Mogul starch molding machine. Such starch molding machines are well known by those of ordinary skill in the art. In one aspect, from 0.3 to 3 grams of the base slurry is deposited into each mold cavity. The starch trays with deposited base slurry are transferred to a drying room where there are held for 12 to 48 hours. Optionally, the trays are first held at a temperature of from 130 to 150° F. for from 10 to 15 hours, and then cooled to 70 to 80° F. and held at that temperature for from 6 to 12 hours. The gelled starch molded food pieces are then removed from the trays, the starch is recycled.

Preferably, the confections of the invention further comprise a sweetener (e.g., a granulated or powder sugar) coating on the exterior surface of the confection. The sweeteners can comprise one or more monosaccharides or disaccharides. Examples include sugar, sucrose, invert sugar, dextrose, lactose, honey, malt syrup, malt syrup solids, maltose, fructose, granular fructose, maple syrup, rice syrup, rice syrup solids, sorghum syrup, refiners syrup, corn syrup, corn syrup solids, high fructose corn syrup, molasses, or combinations thereof. Sanding sugar comprises cane sugar, beet sugar, date sugar, sucanat, granulated fructose or an artificial sweetener (e.g., Sweet-n-Low®, NutraSweet®, or Equal®) and *B. coagulans* in spore form, freeze-dried vegetative cell form, or a combination thereof. Other artificial sweeteners include acesulfame K, aspartame, sucralose, d-tagatose, and combinations thereof.

The probiotic organisms described herein, e.g., *Bacillus coagulans* strain GBI-30 or $BC^{30}$, ATCC Designation Number PTA-6086, uniquely survive the harsh manufacturing and cooking processes of the confection-based compositions. The confection-based compositions are processed for packaging by separating the confection-based compositions from starch (e.g., corn starch). The confection-based compositions are heated to about 100° C. to make them "sticky". Subsequently, the confection-based compositions are placed in a drum tumbler, wherein the probiotic/sugar coating is applied. *Bacillus coagulans* is blended with sugar prior to application to the surface of the confection-based composition. The dry mix for confection-based compositions comprises sugar and an isolated *Bacillus coagulans* bacterium. The dry mix is between 1% and 50% *Bacillus coagulans* bacterium, e.g., about 5%, about 10%, about 15%, about 20%, about 25%, about 35%, about 45%, or about 50% *Bacillus coagulans* bacterium. Preferably, the dry mix is about 15% *Bacillus coagulans* bacterium and 85% sugar. For example, about 100 pounds of dry mix contains about 15 pounds of *Bacillus coagulans* bacterium and about 85 pounds of sugar.

The dry mix is between about 1% and about 50% by weight of the confection-based composition, e.g., about 1% to about 20%, about 5% to about 15%; about 6%, about 7%, about 8%, about 9%, or about 10% by weight of the confection-based composition. For example, a 3 gram confection-based composition contains about 7% dry mix by weight of the confection-based composition. A 3.8 to 4 gram confection-based composition contains about 8-9% dry mix by weight of the confection-based composition.

Alternatively, the isolated *Bacillus coagulans* bacterium is added directly to the confection ingredients prior to heating, molding, and subsequent cooling of the confection. In this manner, the probiotic is introduced into the confection itself, instead of on the surface of the confection-based composition.

As the recommended dietary allowances (RDA or recommended daily intake; RDI) is about $1 \times 10^9$ bacterium (according to EU guidelines), preferably, the confection-based composition comprises at least about $1 \times 10^9$ viable bacteria. In another aspect, the confection-based composition comprises at least about $1 \times 10^6$ to $1 \times 10^7$; at least about $1 \times 10^7$ to $1 \times 10^8$; or at least about $1 \times 10^8$ to $1 \times 10^9$ viable bacteria.

Probiotic Seafood Oil-Based Compositions

The invention is also directed to the surprising discovery that lactic acid-producing bacteria, particularly *Bacillus* species, remain viable and retain their beneficial probiotic properties in seafood/fish oil-based compositions. By "seafood" is meant any fish or shellfish from the sea used for food. Specifically, the probiotic organisms described herein, e.g., *Bacillus coagulans* strain GBI-30 or BC$^{30}$, ATCC Designation Number PTA-6086, survive in the fish oil-based compositions described below. The seafood/fish oil-based compositions are packaged in soft-shelled capsules or soft gelatin capsules or in the form of sugar/gelatin (gummi) confections, e.g., both the *Bacillus coagulans* spores or bacterium and the fish oil are encapsulated together. For example, the fish oil and bacterial spores are incorporated into confection-based compositions, such as the gummi confections described herein. Preferably, the bacterium is present as at least 90% spores, e.g., 95%, 98%, or 99% spores. The fish oil-based compositions are suitable for human or animal consumption. In one aspect, the fish oil-based compositions are administered to children under 18 years of age, e.g., under 15 years of age, under 10 years of age, or under 5 years of age. Alternatively, the fish oil-based compositions are administered to children and adults of all ages.

Fish oil contains two omega-3 fatty acids: eicosapentaenoic acid (EPA; all-cis-5,8,11,14,17-eicosapentaenoic acid) and docosahexaenoic acid (DHA; all-cis-4,7,10,13,16,19-docosahexaenoic acid). Omega-3 fatty acids (n-3 fatty acids or ω-3 fatty acids) are a family of unsaturated fatty acids that have a carbon-carbon double bond at the n-3 position, e.g., at the third carbon bond from the terminal methyl end (n) of the fatty acid. Although fish are a dietary source of omega-3 fatty acids, fish do not produce the fatty acids themselves. Instead, omega-3 fatty acids, such as EPA and DHA are synthesized by microalgae and plankton that live in seawater. Fish accumulate omega-3 fatty acids by either consuming the microalgae that produce the fatty acids, or by eating smaller prey fish that have consumed the omega-3 fatty acids found in microalgae. Thus, fatty predatory fish like mackerel, lake trout, flounder, albacore tuna and salmon possess high levels of omega-3 fatty acids. Krill oil is also a source of omega-3 fatty acids.

The process by which oil is extracted from fish begins with cooking the fish product through a process of steam heating, wherein the fish will reach a top temperature of almost 100° C. This important step not only sterilizes the fish, but also causes the proteins to coagulate and the alteration of cell membranes to aid in the extraction of the oil from the dry material. In some cases, the raw fish is hashed (cut into pieces) prior to steam cooking. After cooking, the mass of fish is pressed or centrifuged to separate the fat-free dry solids (mass of fish) from the liquid (oil & water). This process also creates a fish presscake, which is used by many facilities for the production of fish meal commonly used in animal feed. The liquid collected from mass of fish contains not only water, but also fish oil, salts, proteins, and even undesired waste particles and toxins. The liquid (oil & water) is further filtered to separate the oil and water. At this point, the unrefined fish oil (also referred to as crude fish oil) has not undergone any portion of the refining process.

When fish oil is extracted from fish, so too are the free fatty acids and toxins that are present in the fish. In some cases, fish oils are refined and processed to remove impurities from the fish oil and to enhance the fatty acid potency. Ultra-refined fish oil has been through sophisticated and intensive filtering and refining processes (e.g., winterization) to produce pure and concentrated oil that is as far as possible, free from contaminants. During winterization, the oil is chilled to allow filtration of the saturated fats and particles that form at colder temperatures. Mercury and other metals are subsequently removed before the oil is converted to ethyl esters, subjected to trans-esterification, and molecular or vacuum distillation to remove other fats and undesirable elements and to concentrate the oil. Optionally, fish oil is combined with preservatives and other ingredients suitable for mammalian consumption. For example, in some cases, acid clay is added to remove the pungent smell from the fish oil.

The omega-3 fatty acids derived from the tissues of oily fish, e.g., salmon, herring, anchovies, sardines, tuna, pollock, cod, catfish, flounder, grouper, halibut, mahi mahi, orange roughy, red snapper, shark, swordfish, tilefish, and king mackerel have many health benefits. For example, the omega-3 fatty acids found in fish oil reduce inflammation, slow the spread of cancerous tissue, regulate cholesterol levels, improve cardiovascular health, boost the immune system, and protect the brain from a variety of disorders, such as clinical depression, anxiety, Alzheimer's disease, and Parkinson's disease.

The fish oil-based and confection-based compositions are formulated in many configurations, because the bacterium is present as a vegetative cell or as a spore, or both, depending on the species and form of the probiotic organism. The cells/spores are formulated in a variety of compositions suited for use in a fish oil-based or confection-based composition. In one aspect, the bacterium is present as a mixture of spores and vegetative cells. In another aspect, the bacterium is present as at least 90% spores, e.g., 95%, 98%, or 99% spores. Optionally, prior to addition to the fish oil-based or confection-based compositions of the invention, the *Bacillus coagulans* cells are cultured in liquid in the absence of or with limited quantities of a food source to induce sporulation. In another aspect, heat gun spray drying kills about 50%, about 75%, about 90%, about 95%, or about 99% of vegetative cells prior to addition to the fish oil-based or confection-based compositions of the invention.

In one aspect, *Bacillus coagulans* bacteria in the form of a spray-dried powder is included in or on the surface of the confection-based composition described herein. Preferably, the isolated *Bacillus coagulans* is in the form of a spore. The isolated *Bacillus coagulans* are at least 85%, at least 90%, at least 95%, or at least 99% pure spores. Alternatively, the isolated *Bacillus coagulans* is in the form of a vegetative cell. In one aspect, the isolated *Bacillus coagulans* are at least 85%, at least 90%, or at least 95% pure vegetative cells. In another aspect, the isolated *Bacillus coagulans* is in the form of a mixture of vegetative cells and spores. The *Bacillus coagulans* mixture is 90% spores, 10% vegetative cells; 75% spores, 25% vegetative cells; 60% spores, 40% vegetative cells; 50% spores, 50% vegetative cells; 60% vegetative cells, 40% spores; 75% vegetative cells; 25% spores; or 90% vegetative cells, 10% spores.

The *Bacillus* and/or *Bacillus coagulans* is applied using any of a variety of known methods including, for example, applying a powder, spray-drying the probiotic onto the confection-based composition, or soaking the composition in a solution containing the probiotic. Alternatively, the *Bacillus* bacterium is mixed with the confection ingredients (e.g., gummi ingredients) prior to boiling in water.

Any of a variety of methods for placing the bacterial composition into a fish oil-based or confection-based composition can be used. In one aspect, a "spray-dry" method is used, in which the compositions are exposed in a low humidity chamber to an atomized mix containing a liquid composition, where the chamber is subsequently exposed to approximately 80-110° F. to dry the liquid, thereby impregnating the material of fish oil-based or confection-based composition with the components.

A typical concentration is from approximately $1 \times 10^7$ to $1 \times 10^{12}$ CFU; $1 \times 10^8$ to $1 \times 10^{11}$ CFU; or $1 \times 10^9$ to $1 \times 10^{10}$ CFU of viable bacterium or spores/g of fish oil or confection matrix or sanding sugar. Sanding sugar comprises cane sugar, beet sugar, date sugar, sucanat, granulated fructose or an artificial sweetener (e.g., Sweet-n-Low®, NutraSweet®, or Equal®) and B. coagulans in spore form, freeze-dried vegetative cell form, or a combination thereof. Following drying, the fish oil-based composition or confection is ready for immediate use or for storage in a sterile package, e.g., a 3-ounce package (e.g., a bag or a bottle), a 6-ounce package, a 9-ounce package, a 12-ounce package, a 15-ounce package, an 18-ounce package, or a 24-ounce package.

The active ingredients (i.e., live bacteria or extracellular components), comprise between about 0.01% to about 10%; 0.01% to about 1%; or about 0.05% to about 0.1% by weight of the probiotic fish oil-based or confection-based composition. Optionally, the isolated *Bacillus coagulans* comprise about 1 mg to about 10 g; about 10 mg to about 1 g; or about 25 mg to about 75 mg by weight of the probiotic composition. Most preferably, the amount of *Bacillus coagulans* bacteria is about $5 \times 10^7$ colony forming units (CFU) of bacteria per gram of food matrix.

In one aspect, the amount of bacteria is about $10^4$ to $10^{14}$ colony forming units (CFU) of bacteria per gram of probiotic composition (i.e., vegetative cells and/or bacterial spores), preferably $10^5$ to $10^{13}$ CFU/g of fish oil or confection matrix. Alternatively, the concentrations are $10^8$ to $10^{13}$ CFU/g; $10^9$ to $10^{12}$ CFU/g; or $10^{10}$ to $10^{11}$ CFU/g of fish oil or confection matrix. In one aspect, the amount of bacteria is about $1 \times 10^6$ CFU per gram of fish oil or confection matrix. The actual amount in a fish oil-based or confection-based composition will vary depending upon the amounts of composition to be dispersed into the fish oil or confection composition and upon routes of dispersal.

In one aspect, the invention provides for storing the fish oil-based or confection-based composition in a sterile package at room temperature prior to consumption. Alternatively, the composition is consumed immediately.

By way of example, and not of limitation, *Bacillus coagulans* spores are incorporated into any type of dry or lyophilized product which is dissolved or mixed with hot water, so long as the temperature of the *Bacillus coagulans* spore-containing mixture is raised to the required heat-shock temperature (i.e., 80° C. for 5 minutes) necessary for germination of the spores. The *Bacillus coagulans* spores may either be incorporated into the dry or lyophilized product by the manufacturer of the product or by the consumer during preparation. The fish oil-based or confection-based composition is subsequently boiled in hot water, e.g., stovetop boiling, addition of boiling water to a container, or microwaving the fish oil-based or confection-based composition along with water.

The *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months.

Example 1: Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg MnSO$_4$, and 1,000 ml distilled water, adjusted to pH 7.0, using a standard airlift fermentation vessel at 30° C. The range of MnSO$_4$ acceptable for sporulation is 1 mg/l to 1 g/l. The vegetative cells can actively reproduce up to 45° C., and the spores are stable up to 90° C. After fermentation, the B. coagulans bacterial cells or spores are collected using standard methods (e.g., filtration, centrifugation) and the collected cells and spores can be lyophilized, spray-dried, air-dried or frozen. The supernatant from the cell culture is collected and used as an extracellular agent secreted by B. coagulans.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing B. coagulans Hammer spores at room temperature is about 10 years.

Example 2: Preparation of *Bacillus coagulans* Spores

A culture of dried B. coagulans spores was prepared as follows. Ten million spores were inoculated into a one liter culture containing 24 g potato dextrose broth, 10 g of enzymic-digest of poultry and fish tissue, 5 g of FOS and 10 g MnSO$_4$. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3: *Bacillus coagulans* Spores Survive in the Gastric Environment

This study was performed in order to determine the survivability rate of *Bacillus coagulans* spores as they pass through the stomach. Samples of *Bacillus coagulans* spores were subjected to a simulated gastric environment for varying lengths of time in order to attain their survivability rate. First, a homogeneous sample of raw material *Bacillus coagulans* of at least 12 grams was prepared. Saline solution at pH 1 was prepared using 3N HCl (150 mls each into six 250 ml media bottles) and sterilized. Additional saline solutions with pH 2 and 3 were prepared similarly, resulting in 6 sterile 250 ml bottles, each containing 150 ml pH adjusted saline. Six sterile 250 ml media bottles each containing 150 ml normal saline solution were prepared and sterilized. Phosphate buffer (~400 ml) was prepared at pH 7.2. Test tubes (24) were prepared and sterilized, each containing 9 ml of phosphate buffer pH 7.2. Test tubes (120) were prepared, each containing 9 ml of normal saline. GYE (glucose-yeast extract) agar medium was prepared and sterilized and cooled to 45° C. in a water bath. Samples (24) of raw material were weighed, each~500 milligrams (theoretically equivalent to 10 billion spores). The samples were added to media bottles at 37° C. and incubated half for 20 minutes the other half for 120 minutes. After 20 and 120 minutes incubation, respectively, the samples were mixed to uniformity and pipet 1 ml into 9 ml of sterile phosphate buffer pH 7.2. After all 12 samples from each time point were placed into test tubes containing sterile phosphate buffer, serial dilutions were made until 6 tubes had been used for each sample. The final dilution for the final two test tubes were 3×10$^7$ and 3×10$^8$, which gave a count of roughly 300 and 30 CFU, respectively. The final 2 test tubes from each sample were placed into 70° C. water bath for 30 minutes. After 30 minutes, they were cooled immediately to 45° C. Three sterile petri plates per tube were set out. 1.0 ml from the heat-treated tube was added into each petri plate, then 15 ml of sterile molten GYE Agar medium (at 45° C.) was poured into each of the petri plates and mixed thoroughly. When solidified, the plates were incubated in an inverted position for 48 hours at 40° C. The individual colonies were counted. Results were expressed as CFU per gram as shown in Table 1 below. 1.0E+10=1×10$^{10}$.

TABLE 1

| Sample | 20 Minutes Incubation Spore Count, CFU/gram | 120 Minutes Incubation Spore Count, CFU/gram |
| --- | --- | --- |
| Normal Saline - A | 1.90E+10 | 1.88E+10 |
| Normal Saline - B | 2.12E+10 | 2.00E+10 |
| Normal Saline - C | 1.64E+10 | 2.06E+10 |
| Average | 1.89E+10 | 1.98E+10 |
| Saline pH 1.0 - D | 2.08E+09 | 5.98E+07 |
| Saline pH 1.0 - E | 1.47E+09 | 0.00E+00 |
| Saline pH 1.0 - F | 3.59E+09 | 0.00E+00 |
| Average | 2.38E+09 | 1.99E+07 |
| Saline pH 2.0 - G | 3.63E+09 | 3.46E+09 |
| Saline pH 2.0 - H | 4.47E+09 | 2.48E+09 |
| Saline pH 2.0 - I | 3.58E+09 | 2.82E+09 |
| Average | 3.89E+09 | 2.92E+09 |
| Saline pH 3.0 - J | 1.65E+10 | 1.13E+10 |
| Saline pH 3.0 - K | 1.35E+10 | 1.11E+10 |
| Saline pH 3.0 - L | 1.80E+10 | 1.39E+10 |
| Average | 1.60E+10 | 1.21E+10 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A probiotic oil-based composition, comprising:
   seafood oil, a confection matrix, and isolated *Bacillus coagulans* spores,
   wherein said composition comprises a coating of said isolated *Bacillus coagulans* spores on an exterior surface of said probiotic oil-based composition,
   wherein said isolated *Bacillus coagulans* spores are in an amount from 10$^4$ to 10$^{14}$ colony forming units (CFU) per gram of the seafood oil or the confection matrix,
   wherein said confection matrix is a gelatin-based gummi candy, and
   wherein said isolated *Bacillus coagulans* spores are included as an active ingredient of said gelatin-based gummi candy.

2. The probiotic oil-based composition of claim 1, wherein said seafood oil is selected from the group consisting of salmon oil, cod liver oil, and krill oil.

3. The probiotic oil-based composition of claim 1, wherein said seafood oil is eicosapentaenoic acid or docosahexaenoic acid.

4. The probiotic oil-based composition of claim 1, wherein said isolated *Bacillus coagulans* spores comprise between 0.01% and 10% by weight of said composition.

5. The probiotic oil-based composition of claim 1, wherein said isolated *Bacillus coagulans* spores are selected from the group consisting of GBI-30 strain (ATCC Designation Number PTA-6086), GBI-20 strain (ATCC Designation Number PTA-6085), and GBI-40 strain (ATCC Designation Number PTA-6087).

6. The probiotic oil-based composition of claim 1, wherein said composition comprises said *Bacillus coagulans* spores in the amount from 10$^4$ to 10$^{14}$ colony forming units (CFU) per gram of the confection matrix.

7. The probiotic oil-based composition of claim 1, wherein said composition comprises said *Bacillus coagulans* spores in the amount from 10$^4$ to 10$^{14}$ colony forming units (CFU) per gram of the seafood oil.

8. The probiotic oil-based composition of claim 1, wherein said gelatin-based gummi candy comprises sugar, flavoring, food coloring, and gelatin.

9. The probiotic oil-based composition of claim 1, wherein said gelatin-based gummi candy comprises artificial sweetener, flavoring, food coloring, and gelatin.

* * * * *